United States Patent [19]

Downs et al.

[11] 4,000,209
[45] Dec. 28, 1976

[54] ISOPRENE PRODUCTION AND CATALYST THEREFOR

[75] Inventors: Ronald O. Downs, Creve Coeur, Mo.; James C. Burleson, Friendswood, Tex.

[73] Assignee: Monsanto Company, St. Louis, Mo.

[22] Filed: Nov. 5, 1975

[21] Appl. No.: 628,856

[52] U.S. Cl. .......................... 260/681; 260/680 R; 252/453; 252/455 R
[51] Int. Cl.$^2$ ...................... C07C 1/00; C07C 1/20
[58] Field of Search ................. 260/681, 680 R; 252/453, 455

[56] References Cited

UNITED STATES PATENTS

| | | | |
|---|---|---|---|
| 3,414,588 | 12/1968 | Jones | 260/681 X |
| 3,574,780 | 4/1971 | Watanabe | 260/681 |
| 3,662,016 | 5/1972 | Furuoya et al. | 260/681 |

FOREIGN PATENTS OR APPLICATIONS

| | | | |
|---|---|---|---|
| 45-40521 | 12/1970 | Japan | 260/681 |
| 47-20105 | 9/1972 | Japan | 260/681 |

*Primary Examiner*—Winston A. Douglas
*Assistant Examiner*—John F. Niebling
*Attorney, Agent, or Firm*—J. C. Logomasini; P. L. Passley; N. E. Willis

[57] ABSTRACT

A process for the production of a catalyst for the synthesis of isoprene from isobutylene and formaldehyde which comprises providing a catalyst precursor comprising silica and alumina and modifying the catalyst precursor by treatment with an alkali metal hydroxide and subsequently neutralizing by treatment with a mineral acid, depositing a transition metal on the treated catalyst precursor and calcining to form the catalyst.

5 Claims, No Drawings

ISOPRENE PRODUCTION AND CATALYST THEREFOR

BACKGROUND OF THE INVENTION

This invention relates to the production of isoprene and specifically to a process for the production of isoprene from isobutylene and formaldehyde.

Isoprene is chiefly used as a starting material in the production of synthetic rubbers. As the demand for high quality grades and high volumes of rubber products is increasing, isoprene is becoming a very significant commercial commodity and a cheap and efficient way of producing isoprene would be of great value in the chemical industry.

Many processes for the synthesis of isoprene have been proposed but in many ways the most attractive is that in which isobutylene and formaldehyde are reacted in the presence of a catalyst. Such processes are exemplified by the disclosures in U.S. Pat. Nos. 3,662,016; 3,146,278; 3,437,711 and 3,621,072. Catalyst proposed in the prior art include alumina, silica/alumina, phosphoric acid in conjunction with chromium oxide or manganese dioxide, a mixture of silica and antimony oxide, and phoshoric acid treated with a group II metal oxide or hydroxide.

However, it is found that the prior art catalysts often produce undesirably large quantities of by-products such as polymerized isobutylene. There is, therefore, a need for a catalyst having improved selectivity towards the desired product.

A modified catalyst has now been discovered that has such increased selectivity to isoprene while retaining a high conversion rate.

Thus the present invention has as its primary object the provision of a process for the production of a novel catalyst suitable for use in the reaction of isobutylene with formaldehyde to produce isoprene.

A further object of the present invention is to provide a process for the production of isoprene using such novel catalyst.

SUMMARY OF THE INVENTION

This invention, therefore, provides a process for the production of a catalyst suitable for use in synthesis of isoprene from isobutylene and formaldehyde which comprises providing a catalyst precursor comprising silica and alumina and modifying the catalyst precursor by treatment with an alkali metal hydroxide, neutralizing the catalyst precursor by treatment with a mineral acid, depositing a transition metal compound on the treated catalyst precursor and calcining to form the catalyst.

As indicated above a further aspect of the present invention is the provision of a process for the production of isoprene in which isobutylene and formaldehyde are reacted at a temperature of from 250° to 450° C in the presence of a catalyst comprising silica and alumina that has previously been treated with an alkali metal hydroxide, neutralized using a mineral acid, and treated with a transition metal compound.

While the mechanism of the silica/alumina catalyst precursor modification process has not been fully elucidated it appears that the catalyst precursor comprises a number of Lewis acid sites and if these are present in large quantities the catalyst is excessively active and lacks selectivity. The object of the modification treatment disclosed herein is to modify the Lewis acid sites by reaction with the alkali metal hydroxide thus creating more Bronsted acid sites and thereafter to restore substantial neutrality by treatment with mineral acid and to increase the surface area of the catalyst by partial solution of the alumina.

The catalyst precursor used is, as has been explained, one comprising silica and alumina. Examples of suitable catalyst precursors include commercial silica/aluminas having a silica to alumina weight ratio of from 2:1 to 10:1 (such as for example the catalyst base material sold by Houdry as S.90 which has a $SiO_2/Al_2O_3$ weight ratio of 7.2:1), a natural or synthetic zeolite, and an alumina-silicate mineral such as attapulgite. In preferred catalyst precursors the silica and alumina are present in a Si:Al ratio of about 4:1 to 10:1 and preferably from 5:1 to 8:1.

The alkali metal hydroxide used to treat the catalyst precursor can be selected from any of the hydroxides of the alkali metals of Group 1A of the Periodic Table, but the most suitable hydroxide is found to be potassium hydroxide. The amount of the hydroxide used is not critical, but it is generally preferred that it be used in an excess over the amount necessary to neutralize the Lewis acid sites. As a guide to the amount to be used in practice, it is convenient that 2 to 5 grams and preferably 3 to 4 grams of alkali metal hydroxide be added to every 10 grams of catalyst precursor. Of course, care must be taken to ensure that the structure of the catalyst is not totally broken down by solution of the alumina to form an aluminate. Some loss of aluminum is, however, desirable to increase the surface area of the catalyst base. In general, the molar ratio of silica to alumina is increased by from 50 to 150% and preferably by about 100% during the treatment with the alkali metal hydroxide.

The mineral acid used to neutralize the modified catalyst precursor can be, for example, sulphuric, nitric, hydrochloric, hydrobromic, or phosphoric acid, but the preferred acid is sulphuric acid. The amount of acid used is that required to bring about substantial neutrality in the modified catalyst precursor. The actual quantity, therefore, depends on the amount of alkali used. In practice, the treatment is discontinued when a water wash of the neutralized catalyst precursor shows a pH of about 6 to 7.

It is convenient to dry the modified catalyst precursor in, for example, a muffle oven before treating it with the transition metal compound.

The transition metal is deposited by a suitable means, on modified catalyst precursor in the form of a salt of the transition metal which is then calcined to convert the salt into the oxide form.

The amount of transition metal (measured as the oxide) incorporated in the catalyst precursor is not critical and can range from about 0.1% to 4% of the total catalyst weight. It is, however, preferred that from 0.5% to 3% and most preferably from 1% to 2% of the total catalyst weight is provided by the transition metal (measured as the oxide).

The transition metal is usually selected from those well known in the art to have substantial catalytic activity such as, for example, chromium, iron, cobalt, nickel, vanadium manganese, tungsten, iridium and platinum. However, from among these metals, tungsten is found to be particularly useful.

The salt used to incorporate the metal into the catalyst precursor should preferably be one that will not, on conversion to the oxide, release by-products that might poison the catalyst. In general, halides, nitrates and carboxylates can be used with the chloride being particularly preferred. Thus, with the preferred transition metal, the preferred salt is tungsten hexachloride.

The incorporation of the transition metal into the modified catalyst precursor is preferably done in such a way that the transition metal is finely and evenly distributed over the precursor surface and still more preferably in such a way that the metal becomes bonded to the precursor such that the catalyst can withstand prolonged heating under reaction conditions and periodic regeneration cycles in which it may be heated in air at temperatures up to 1000° C without loss of the transition metal.

The transition metal is usually added to the precursor in the form of a solution. Since water hydrolyses many of the possible salts that could be used, it is usually preferred that the solution be made up in an organic solvent such as a liquid saturated hydrocarbon or a petro-ether solvent. A very useful solvent has been found to be cyclohexane, though other organic solvents can be used if they are able to dissolve the transition metal salt without impairing its ability to bond to the precursor.

While the mechanism is not fully understood, it would appear that the transition metal salt becomes attached to oxygen atoms in the precursor through chemical bonds when the transition metal salt is decomposed to form the oxide.

Though it is preferred that the transition metal salt be deposited on the precursor by treating the precursor with a solution of the salt, it is possible to arrange that the salt be deposited on the precursor by vapor deposition or by treatment with a fine dispersion in a suitable liquid carrier. Such methods, however, would be more difficult and could be defective in stability under regeneration conditions and uniformity of the treatment of the catalyst precursor surface.

After incorporation of the transition metal salt, the catalyst precursor is calcined to convert the salt to the oxide and give the finished catalyst. This operation is most usually performed in air and to accomplish the desired conversion it is usually necessary to heat for 30-90 minutes at above 450° C and preferably at from 500° to 700° C, though higher temperatures can be used if desired.

The catalyst can be used in the production of isoprene from isobutylene and formaldehyde in any of the conventional gas phase catalytic reaction vessels known in the art. Thus the catalyst may be in a fixed or fluidized bed reactor of any desired configuration. The gaseous reactants are passed over the catalyst at a temperature of from 250° to 450° C and preferably from 300° to 350° C. The pressure is conveniently about atmospheric though higher pressures, for example up to 8.0 kg/cm$^2$ can often be used with advantage. After passage of the reactants through the reactor it is often convenient to separate the product isoprene and recycle the gaseous residues through the reactor.

The invention is further illustrated by the following Examples which are not, however, to be taken as implying any limitation of the scope thereof. Unless otherwise stated, all parts given are by weight.

PREPARATION OF THE MODIFIED CATALYST

EXAMPLE 1

156.7 grams of pellets of a silica/alumina catalyst precursor having a silica/alumina weight ratio of 7.2:1 and having a mesh size of 12-30 were treated with 60 grams of potassium hydroxide dissolved in 200 ml. of water.

After treatment, the pellets were washed six times with 300 to 400 ml of water. The last wash had a pH of 8-9 showing that the pellets were still basic. The pellets were then treated with 105 grams of sulfuric acid in aqueous solution and were then washed as above until the pH of the wash was 6. The pellets were then dried in a muffle oven at 600° C.

Before treatment the catalyst precursor pellets had a surface area per gram of 296 sq. meters and a ratio of silica to alumina of 7.2 (as determined from relative numbers of silicon and aluminum atoms measured by X-ray fluorescence).

After treatment, due to the solution of some of the aluminum by the alkali, the ratio of silica to alumina was 15.8 and the surface area was 531 square meters per gram.

24.4 grams of the treated catalyst precursor prepared were treated with a solution of 0.42 gram of tungsten hexachloride in 100 ml of cyclohexane. The mixture was initially brown and then turned blue. After separation and calcination in air for about an hour at 600° C, the modified catalyst was found to contain 1% of tungsten oxide ($WO_3$).

EXAMPLE 2

25.5 grams of the treated catalyst precursor were treated with 0.22 gram of tungsten hexachloride as described in Example 1. The separated catalyst was found to contain 0.5% of tungsten oxide.

EXAMPLE 3

25 grams of the treated catalyst precursor were treated with 0.84 gram of tungsten hexachloride as described in Example 1. The separated catalyst was found to contain 2.0% of tungsten oxide.

PRODUCTION OF ISOPRENE

EXAMPLE 4

Isoprene was prepared using the catalysts prepared by the methods described in Examples 1 to 3. In each case the catalyst was placed in a reactor in the form of a stainless steel tube with an outside diameter of 1.26 cm and a length of 22.8 cm maintained at a temperature of 325°-335° C. The catalyst volume was 0.02 liter, and the catalyst was in the form of 12-30 mesh particles. The runs took approximately 53½ minutes, and the contact time that is the estimated time that each molecule of the reactants took to pass through the reactor in contact with the catalyst was approximately 0.3 seconds.

Isobutylene and formaldehyde (the latter being supplied in the form of an aqueous solution-(formalin)-containing 37% by weight of formaldehyde), were mixed, passed through a vaporizer to vaporize the formalin and raise the mixture to the reaction temperature and then through the reactor containing the catalyst.

The product gases from the reactor were analyzed to determine the conversion of isobutylene and formaldehyde and the yield of isoprene, and the results are shown on Table 1.

TABLE 1

| Catalyst | Reactor Temp | Run Time Mins. | Press Kg/cm² | Feedstock(Moles) i–C₄+ | CH₂O ++ | Selectivity % i–C₄ | CH₂O | Conversion % i–C₄ | CH₂O | Productivity (i–C₅)+++ g/hr/g |
|---|---|---|---|---|---|---|---|---|---|---|
| Ex 1 | 325 | 53.7 | .13 | 4.38 | .35 | 88 | 95 | 23 | 84 | .99 |
| Ex 2 | 330 | 53.6 | .15 | 4.37 | .35 | 59 | 86 | 20 | 88 | .87 |
| Ex 3 | 335 | 54.4 | .13 | 4.35 | .35 | 85 | 94 | 18 | 84 | .85 |

+ i–C₄ = isobutylene
++ CH₂O = formaldehyde
+++ i–C₅ = isoprene

COMPARATIVE EXAMPLE

The treated catalyst precursor described in Example 1 (i.e., minus the treatment with tungsten hexachloride) was placed in a reactor 22.8 cm in length and maintained at a temperature of 300° C. The catalyst volume was 0.023 liters.

A flow of 0.0815 mole/min of isobutylene and 0.0065 mole/min of formaldehyde was passed through the reactor and the pressure was maintained at about atmospheric.

The reaction time was 45.3 minutes and the product gases from the reactor were analyzed to determine the conversion of isobutylene and formaldehyde and the yield of isoprene.

It was found that the conversion of formaldehyde was 82% with 80% selectivity, the conversion of isobutylene was 7% with 62% selectivity, and the productivity of isoprene from the reaction was 0.249 gram/hr/gram.

From the above Examples it will be seen that the deposition of the tungsten compound on the modified catalyst according to the invention results in a catalyst having an improved conversion rate and generally higher selectivity towards both reactants and excellent productivity in the conversion of isobutylene and formaldehyde to isoprene.

What is claimed is:

1. A process for the production of isoprene which comprises reacting isobutylene and formaldehyde at a temperature of from 250° to 450° C in the presence of a catalyst produced by a process which comprises;
    a. treating a catalyst precursor comprising silica and alumina in a weight ratio of from 2:1 to 10:1 with an alkali metal hydroxide;
    b. neutralizing the treated catalyst precursor with a mineral acid; and
    c. forming the catalyst by depositing a transition metal salt on the neutralized catalyst precursor and calcining the thus treated precursor under such conditions as to convert the transition metal salt to the oxide, the amount of transition metal salt added being such that the amount of transition metal oxide in the catalyst is from 0.1 to 4% of the catalyst weight.

2. A process according to claim 1 in which the isobutylene and formaldehyde are reacted at a temperature of from 300 to 350° C.

3. A process according to claim 1 in which the catalyst precursor has a silica/alumina weight ratio of from 5:1 to 8:1 before treatment with the alkali metal hydroxide.

4. A process according to claim 1 in which the catalyst precursor is treated with from 3 to 4 grams of potassium hydroxide for every 10 grams of catalyst precursor and neutralized with sulfuric acid.

5. A process for the production of isoprene which comprises reacting isobutylene and formaldehyde at a temperature of from 300° to 350° C in the presence of a catalyst prepared by a process which comprises;
    a. treating a silica/alumina catalyst precursor having a silica/alumina weight ratio of from 5:1 to 8:1 with from 3 to 4 grams of potassium hydroxide for every 10 grams of catalyst precursor;
    b. neutralizing the treated catalyst precursor with sulfuric acid;
    c. forming the catalyst by treating the neutralized catalyst precursor with a solution in cyclohexane of tungsten hexachloride and calcining the thus treated precursor under such conditions as to convert the tungsten hexachloride to the trioxide, the amount of tungsten hexachloride added being such that the amount of tungsten trioxide in the catalyst is from 0.5 to 2.0% of the catalyst weight.

* * * * *